US005724432A

United States Patent [19]

Bouvet et al.

[11] Patent Number: 5,724,432

[45] Date of Patent: Mar. 3, 1998

[54] ACOUSTIC ATTENUATION DEVICE WITH ACTIVE DOUBLE WALL

[75] Inventors: Pascal Bouvet, Lyons; Jacques Roland, Corenc; Laurent Gagliardini, Paris, all of France

[73] Assignee: Centre Scientifigue et Technique du Batiment, Paris, France

[21] Appl. No.: 535,067

[22] PCT Filed: May 4, 1994

[86] PCT No.: PCT/FR94/00520

§ 371 Date: Feb. 15, 1996

§ 102(e) Date: Feb. 15, 1996

[87] PCT Pub. No.: WO94/27283

PCT Pub. Date: Nov. 24, 1994

[30] Foreign Application Priority Data

May 6, 1993 [FR] France .................................. 93 05451

[51] Int. Cl.$^6$ ............................ H04B 15/00; A61F 11/06

[52] U.S. Cl. ................................................ 381/71; 381/94

[58] Field of Search ........................................ 381/71, 94

[56] References Cited

U.S. PATENT DOCUMENTS

| | | | |
|---|---|---|---|
| 4,947,356 | 8/1990 | Elliott | 381/71 |
| 5,024,288 | 6/1991 | Shepherd et al. . | |
| 5,245,552 | 9/1993 | Andersson | 381/71 |
| 5,315,661 | 5/1994 | Gossman et al. . | |
| 5,627,897 | 5/1997 | Gagliardini et al. | 381/71 |

FOREIGN PATENT DOCUMENTS

| | | | |
|---|---|---|---|
| 0041260 | 12/1981 | European Pat. Off. . | |
| 3095349 | 7/1991 | Japan . | |
| 5173580 | 7/1993 | Japan | 381/94 |
| 6242786 | 9/1994 | Japan | 381/71 |

OTHER PUBLICATIONS

Patent Abstracts of Japan, vol. 015, No. 276 (M-1135) 12 Jul. 1991 for: JP.A.03.095.349 (Hitachi Plant Eng & Constru Co Ltd).

Journal of the Acoustical Society of America, vol. 92, No. 3, Sep. 1992, New York US, pp. 1521-1533, Clark et al., 'Optimal placement of piezoelectric actuators and polyvinylidene fluoride error sensors in active structural acoustic approaches'.

WO 94 05005, Noise Cancellation Technologies, 3 Mar. 1994.

*Primary Examiner*—Curtis Kuntz
*Assistant Examiner*—Xu Mei
*Attorney, Agent, or Firm*—Henderson & Sturm

[57] ABSTRACT

An active double wall comprises two parallel plates defining a rectangular space. Four sensors are positioned between the plates so as to detect noises in said space, and four actuators are placed between the plates to emit counter-noises in the space. The actuators are phase-controlled by a control unit in order to minimize the sum of the outputs of the sensors. The actuators are respectively positioned at the centers of the sides of the rectangular space, and the sensors are respectively positioned at the centers of the sides of a rhombus whose vertices are the respective centers of the sides of the rectangular space, or vice-versa.

17 Claims, 2 Drawing Sheets

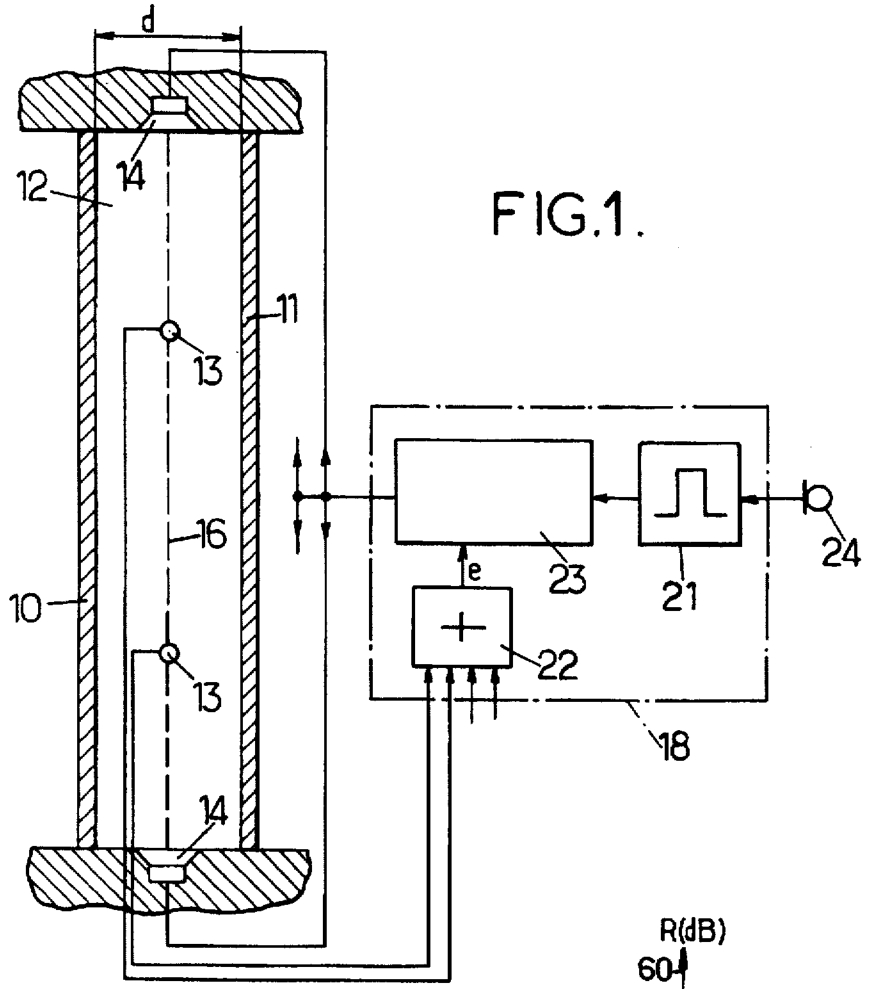
FIG.1.
FIG.2.
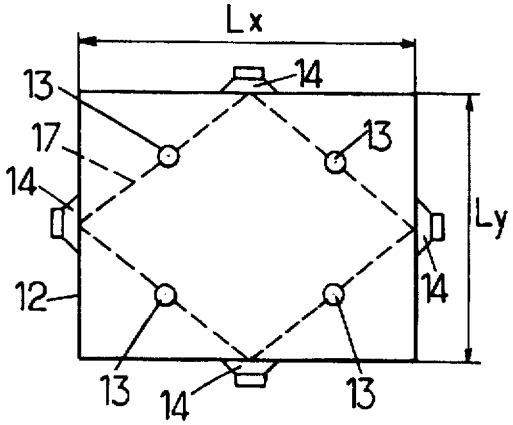
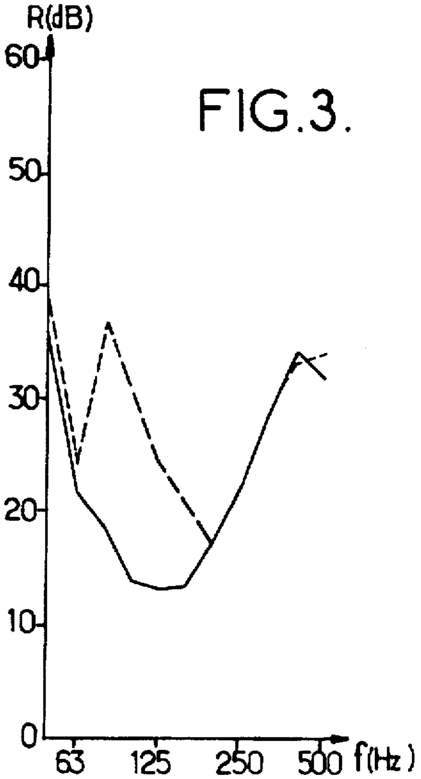
FIG.3.

ACOUSTIC ATTENUATION DEVICE WITH ACTIVE DOUBLE WALL

BACKGROUND OF THE INVENTION

The present invention relates to an acoustic attenuation device, comprising two substantially parallel plates defining a rectangularly shaped space, noise detection means arranged between the two plates, inverse noise emission means arranged between the two plates, and control means for controlling the inverse noise emission means in such a way as to minimize a quantity supplied by the noise detection means.

Applications of the invention are, for example, in the field of sound insulation of premises, in particular with double glazing, in the production of cowlings for equipment that generates noise, or in the field of insulating the passenger compartments of means of transport.

A device of the type indicated above, termed active double wall, relies on the operating principle summarized below.

The mass-spring-mass resonant frequency of a double wall constituted by two parallel rectangular plates separated by an air sheet of thickness d is given by the equation:

$$f_{mm} = \frac{1}{2\pi}\sqrt{\frac{\rho_0 c_0^2}{d}\left(\frac{1}{m_1}+\frac{1}{m_2}\right)} \quad (1)$$

with:

- $\rho_0$: density of the medium located between the plates (1.18 $Kg/m^3$ in the case of air)
- $c_0$: speed of sound in the medium located between the plates (340 m/s in the case of air).

$$\frac{\rho_0 c_0^2}{d}:$$

stiffness of the air sheet $m_1$, $m_2$: mass per unit area of the plates (in $kg/m^2$)

This resonant frequency generally lies between 50 and 250 Hz.

Overall, for a given frequency f, the acoustic behavior of a double wall is considered to be as follows:

- $f<f_{mrm}$: the two plates vibrate in phase. The variation in volume between the plates remains small. The double wall behaves as a single wall of equivalent mass.
- $f\approx f_{mrm}$: the two plates, strongly coupled by the air sheet, vibrate in phase opposition. This leads to large variations in volume of the air sheet (phenomenon of "breathing" of the plates) and to poor acoustic insulation by the double wall.
- $f>f_{mrm}$: the movements of the two plates are decoupled by the air sheet. The acoustic insulation of the wall then increases rapidly with frequency.

The attenuation device aims to compensate for the poor acoustic insulation provided by the double wall close to $f_{mrm}$. The principle consists in preventing, by means of an electro-acoustic system, any variation in volume of the air sheet.

The acoustic pressure field in the air sheet can be written in the form of a modal series:

$$p(x,y,z,t) = \sum_{l=0}^{\infty}\sum_{m=0}^{\infty}\sum_{n=o}^{\infty} \alpha_{lmn}\phi_{lmn}(x,y,z)\cdot e^{j\omega t} \quad (2)$$

with:

- $\alpha_{1mn}$: amplitude of mode 1,m,n
- $\varnothing_{1mn}$: modal base associated with the cavity in question.

In the case of a parallelepipedally shaped air sheet:

$$\varnothing_{lmn}(x,y,z)=\cos(1\pi x/L_x)\cos(m\pi y/L_y)\cos(n\pi z/L_z) \quad (3)$$

- $L_x$, $L_y$, $L_z$ (=d): dimensions of the air sheet
- ω: angular frequency (=2πf)
- x,y: spatial coordinates parallel to the plates
- z: spatial coordinate perpendicular to the plates
- t: time.

The eigenfrequency $f_{lmn}$ of a mode with indices (l,m,n) of the air sheet is given by the equation:

$$f_{lmn} = \frac{c_0}{2\pi}\sqrt{\left(\frac{1\pi}{L_x}\right)^2+\left(\frac{m\pi}{L_y}\right)^2+\left(\frac{n\pi}{L_z}\right)^2} \quad (4)$$

The variation in volume of the air sheet is directly proportional to the amplitude of the (0,0,0) mode, without the amplitude of the other modes close to the resonant frequency $f_{mrm}$ of the wall being affected. However, it is difficult to measure and excite only this mode by actions which, a priori, involve all the modes. Indeed, the expression given above (2) for the acoustic pressure shows that the measurement taken by a microphone will include the responses of modes other than the (0,0,0) mode.

It is desirable, in order to obtain efficient attenuation, to reduce the contribution, in the quantity to be minimized, of the low-frequency modes other than the (0,0,0) mode, and to operate so that the inverse noise emission means excite the (0,0,0) mode predominantly while exciting the other modes of the air sheet as little as possible.

One object of the invention is thus to improve the efficiency of the attenuation provided by an active double wall device.

SUMMARY OF THE INVENTION

To this end, the invention provides an acoustic attenuation device of the type indicated at the start, characterized in that the inverse noise emission means comprise four actuators whose respective positions parallel to the plates correspond approximately to the four points constituting the centers of the sides of the rectangular shape of said internal space, in that the noise detection means comprise four sensors whose respective positions parallel to the plates correspond approximately to the four points constituting the centers of the sides of a rhombus whose vertices are the centers of the sides of the rectangular shape of said internal space, in that the four actuators are controlled in phase, and in that the quantity to be minimized is represented by the sum of the output signals of the four sensors.

With this arrangement, the sensors and the actuators interact practically not at all with the odd-order modes of the space located between the two plates (i.e. the modes whose indices are of type (l,m,n) with l or m odd), or with the (0,2,0) and (2,0,0) modes. Satisfactory control of the (0,0,0) mode can therefore be obtained without substantially affecting the efficiency of the attenuation by exciting the low-eigenfrequency modes.

Furthermore, with this embodiment of the invention, the actuators are advantageously located at the periphery of the double wall.

In another embodiment of the invention, relying on the same principle, the respective positions of the sensors and of the actuators are reversed, i.e. the noise detection means comprise four sensors whose respective positions parallel to the plates correspond approximately to the four points constituting the centers of the sides of the rectangular shape of the said internal space, and the inverse noise emission means comprise four actuators whose respective positions parallel to the plates correspond approximately to the four points constituting the centers of the sides of a rhombus whose vertices are the centers of the sides of the rectangular shape of said internal space.

It has also been observed that it was advantageous for a gas lighter than air, for example helium, to occupy the internal space located between the two plates. This decrease in the density of the medium located between the plates leads to an increase in the speed of sound in this medium and therefore to an increase in the eigenfrequencies associated with the various modes (cf. formula (4)). The result of this is a lower contribution to acoustic transmission by the modes other than the (0,0,0) mode, and therefore better attenuation by the selective control of the (0,0,0) mode.

BRIEF DESCRIPTION OF THE DRAWINGS

FIG. 1 schematically represents an acoustic attenuation device according to the invention;

FIG. 2 is a schematic view illustrating the positions of the sensors and of the actuators of the device in FIG. 1;

FIG. 3 is a graph showing the acoustic attenuation which a device such as that in FIGS. 1 and can provide;

DESCRIPTION OF PREFERRED EMBODIMENTS

Figure 4:
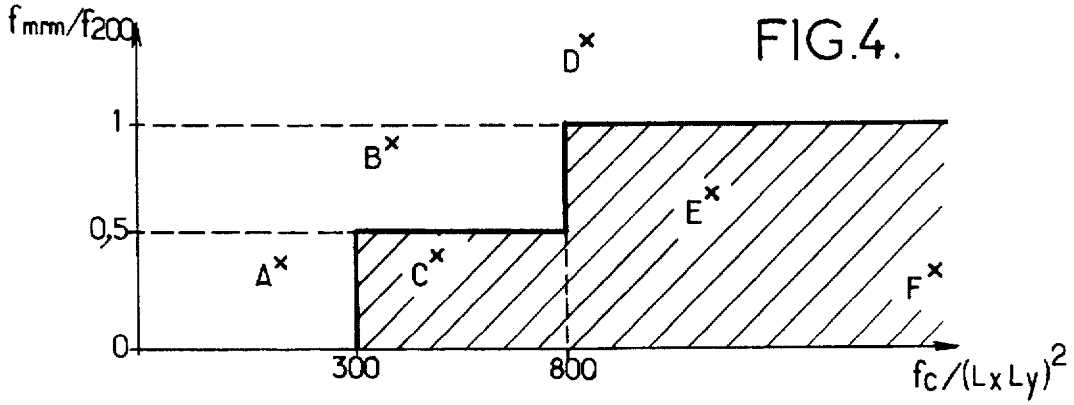
FIG. 4 is a graph illustrating a preferred parameter range in a device according to the invention.
Figure 5A:
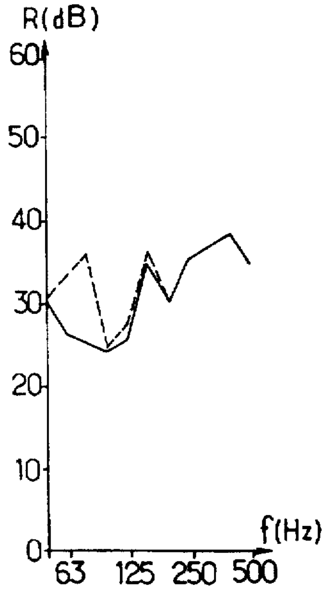
FIGS. 5A to 5F are graphs showing the acoustic attenuation which can be obtained with various examples of composition of the plates.
Figure 5B:
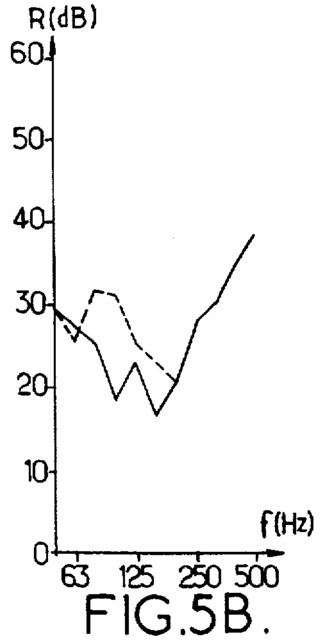
Figure 5C:
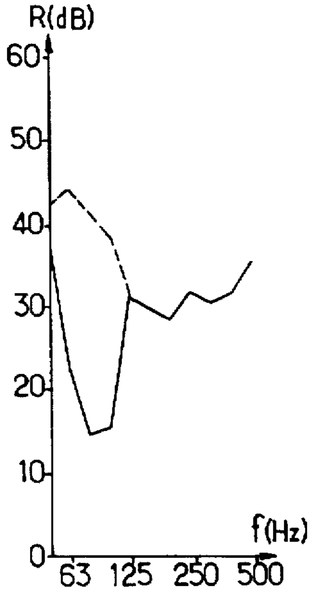
Figure 5D:
Figure 5E:
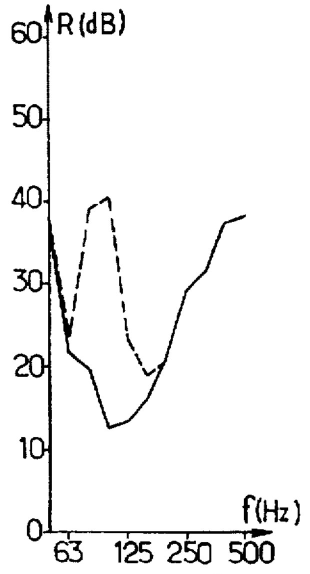
Figure 5F:
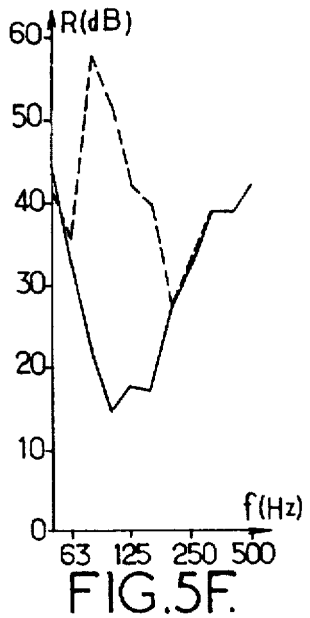

The device represented in FIG. 1 constitutes an active double wall which can be used to provide acoustic insulation between the spaces located on either side of the wall. The wall comprises two parallel rectangular plates 10, 11 which define between them a rectangularly shaped internal space 12. Sensors 13 and actuators 14 are arranged between the two plates 10, 11 in order respectively to detect the noise existing in the space 12 and to emit inverse noise into the space 12.

The actuators 14 are placed on the edges of the internal space 12, while the sensors are mounted on a wire mesh 16 fitted between the plates 10, 11. The arrangement of the sensors 13 and of the actuators 14 parallel to the plates is illustrated in FIG. 2. There are four actuators 14 and they are arranged at the four points constituting the centers of the sides of the rectangular space 12. There are four sensors 13 and they are arranged at the four points constituting the centers of the sides of a rhombus 17 whose vertices are the centers of the sides of the rectangular space 12.

The sensors 13 may be electret microphones chosen to have sensitivity and phase characteristics that do not vary by more than 1% from one sensor to another. The actuators 14 may be loudspeakers. An example of a loudspeaker that can be used is the model AUDAX BMX 400 which represents a good compromise between volume output and size (rated power 15 W, resonant frequency of the order of 150 Hz, external diameter 77.8 mm, total mass 290 g).

A control unit 18 and [sic] provided for controlling the actuators 14 in such a way as to minimize an error signal e supplied by the sensors 13. The error signal to be minimized is constituted by the amplified sum of the output signals of the four sensors 13, which is delivered by an adder 22. The control unit 18 comprises a signal processor 23 programmed in known fashion to apply the gradient algorithm (LMS) with filtered reference. This adaptive filtering mode with finite impulse response is well known in the field of noise cancellation (see, for example, the works "Traitement numérique du signal" [Digital signal processing] by M. Bellanger, Editions Masson, Paris 1981; and "Adaptive signal processing" by B. Widrow and S. D. Stearns, Prentice Hall, 1985). A reference microphone 24, located on the side of the source of noise to be attenuated, supplies a reference signal which is applied to a bandpass filter 21 whose output, sent to the processor 23, is subjected to the finite impulse response filtering. The coefficients of the filter are updated on each sampling cycle in order to minimize the error signal e. The processor 23 then sends the same control signal to the actuators 14, so that the actuators 14 are controlled in phase.

In a typical exemplary embodiment, the two plates 10, 11 are made of plexiglass and have mass per unit area $m_1=m_2=6$ kg/m$^2$. They define an internal space 12 of thickness d=5 cm, the rectangular shape of which has sides of length $L_x=1.6$ m and $L_y=1.2$ m. Since the space 12 is filled with air, the mass-spring-mass resonant frequency (formula (1)) is equal to $f_{mrm}=150$ Hz. The critical frequency of the plates is 6400 Hz. The resonant frequencies of the first even modes of the air sheet (formula (2)) are given in table I.

TABLE I

| (l,m,n) | (2,0,0) | (0,2,0) | (2,2,0) | (4,0,0) | (4,2,0) |
|---|---|---|---|---|---|
| $f_{lmn}$ (Hz) | 216 | 290 | 362 | 434 | 522 |

The sum of the output signals of the four sensors, which represents the signal e to be minimized, reflects the response of the (0,0,0) mode of the space 12 located between the plates 10, 11. In the error signal e, there is practically no contribution from the odd-order modes (l, m, n) with l or m odd, in view of the symmetrical arrangement of the sensors, or from the even-order modes of relatively low eigenfrequency (2,0,0), (0,2,0) and (0,2,0). Apart from the (0,0,0) mode, the mode contributing to the signal e and having the lowest eigenfrequency is the (4,0,0) mode. However, the eigenfrequency of this mode is relatively far from the resonant frequency $f_{mrm}$, so that the influence of this mode and of the higher-index modes on the acoustic transmission is not dominant.

Because of their positions, the actuators controlled in phase excite the odd-order modes and the (2,0,0) and (0,2,0) modes practically not at all. Thus, the excitation of the actuators 14 acts mainly to compensate the transmission by the (0,0,0) mode without substantially increasing the amplitudes of the other low-eigenfrequency modes.

FIG. 3 shows the results of simulations of the acoustic attenuation provided by the device in FIG. 1 (without the filter 21) in the example of the parameters indicated above. The broken-line curve corresponds to the values of the attenuation coefficient R as a function of the frequency f of the noise to be attenuated in the case when there is active control of the (0,0,0) mode, and the solid-line curve corresponds to the same values in the absence of active control. It is seen that the active control according to the invention substantially increases the attenuation coefficient in the range of low frequencies close to the resonant frequency $f_{mrm}$.

For the frequencies far from $f_{mrm}$, there is not always an improvement in the attenuation coefficient and, in certain cases, a slight deterioration may even be produced. This is why the band-pass filter 21 is provided in the control unit 18. This filter 21, to which the reference signal is applied before the finite impulse response filtering, allows those frequencies for which control of the (0,0,0) mode has a favorable effect on the attenuation coefficient to pass, that is to say the frequencies between $f_{mrm}/2$ and min(2 $f_{mrm}$, $f_{200}$), $f_{200}$ denoting the smaller eigenfrequency of the even-order modes: $f_{200}=c_0/\max(L_x, L_y)$, where $c_0$ denotes the speed of sound in the medium located between the two plates 10, 11.

It will be understood that various modifications of the example described above with reference to FIG. 1 and 2 are envisageable without departing from the scope of the invention.

Thus, it is possible to reverse the respective positions of the sensors and actuators (FIG. 2) while obtaining equally good selective control of the (0,0,0) mode. It is also possible to line the interior of the plates with a sound insulator such as glass wool. A control mode other than adaptive filtering may further be used.

In a particularly advantageous embodiment, the space 12 located between the plates 10, 11 is occupied by a gas lighter than air. This increases the speed of sound in the medium located between the plates, which decreases the density of the eigen modes at low frequencies (formula (4)), while the resonant frequency $f_{mrm}$ is modified only a little. The relative contribution of the (0,0,0) mode to the acoustic transmission is then increased, so that the efficiency of the active control of this mode is improved. The effect of this becomes more marked as the mass of the gas decreases. Helium is therefore a preferred example for this gas. This effect is also produced for configurations of the sensors and actuators other than that represented in FIG. 2. Thus, in the case of the double wall indicated above by way of example and with a configuration having four sensors and a central actuator, the Applicant experimentally measured the mean attenuation coefficients $R_m$ in dB(A) which are given in table II when the space 12 is filled with air or helium. These measurements were taken with two types of noise to be attenuated: pink noise and road noise. It is observed that the improvement in attenuation provided by helium is markedly greater when active control of the (0,0,0) mode is employed.

TABLE II

| | | pink noise $R_m$ (dB (A)) | road noise $R_m$ (db (A)) |
|---|---|---|---|
| air | without active control | 33 | 27 |
| | with active control | 40 | 35 |
| helium | without active control | 35 | 28 |
| | with active control | 49 | 43 |

The Applicant performed numerous simulations in order to determine the plate parameters giving rise to good acoustic attenuation by (0,0,0) mode control. In FIG. 4, the range of parameters providing the best attenuation characteristics is represented by hatch marks. The range corresponds to the compositions of the plates for which the acoustic transmission around the resonant frequency $f_{mrm}$ is essentially governed by the (0,0,0) mode. It corresponds to the relationships:

$$f_c/(L_xL_y)^2>800 \text{ and } f_{mrm}<f_{200} \quad (5)$$

or $$f_c/(L_xL_y)^2>300 \text{ and } f_{mrm}<f_{200}/2, \quad (6)$$

in which $f_c$, in hertz, denotes the critical frequency of a plate or, if the plates 10, 11 are of different compositions, the higher of the critical frequencies of the two plates (in the case of a homogeneous plane plate, the critical frequency is equal to $$f_c=\frac{C^2}{2\pi}\sqrt{m/D}$$

with C=speed of sound in air, m=mass per unit area of the plate, $D=Eh^3/12(1-\nu^2)$=bending stiffness of the plate, E=Young's modulus, ν=Poisson's coefficient, h =thickness of the plate);

$L_x$ and $L_y$ are the lengths, expressed in meters, of the sides of the rectangular space;

$f_{mrm}$ is the mass-spring-mass resonant frequency given by formula (1); and $f_{200}=c_0/\max(L_x,L_y)$ is the eigenfrequency of the even mode of the cavity having the lower eigenfrequency.

Examples of attenuation curves (attenuation coefficient R as a function of frequency) obtained by simulating various compositions of the plates are represented in FIGS. 5A to 5F, which respectively correspond to the points A to F on the diagram in FIG. 4. The solid-line curves illustrate the attenuation coefficient in the absence of active control, and the broken-line curves illustrate the attenuation coefficient simulated by subtracting the contribution of the (0,0,0) mode. The configurations of the plate are presented in table III below.

It can be observed in FIGS. 5A to 5F that the cases (C, E and F) for which relationships (5) or (6) are satisfied are those leading to the greatest improvement in the attenuation around the resonant frequency $f_{mrm}$. Active control using a configuration of sensors and actuators which provides a satisfactory approximation of the (0,0,0) mode will lead to a substantial improvement in the attenuation when the materials and the dimensions of the plates obey relationships (5) or (6).

TABLE III

| Figure | | 5A | 5B | 5C | 5D | 5E | 5F |
|---|---|---|---|---|---|---|---|
| plate material | | chipboard | glass | chipboard | steel | steel | steel |
| m | (kg/m²) | 15.6 | 11.7 | 15.6 | 11.7 | 7.8 | 7.8 |
| $L_xL_y$ | (m²) | 2 | 3 | 1.3 | 3 | 2 | 0.7 |
| d | (m) | 0.05 | 0.025 | 0.05 | 0.012 | 0.05 | 0.05 |
| $f_c/(L_xL_y)^2$ | (Hz/m⁴) | 230 | 440 | 550 | 900 | 3000 | 24000 |
| $f_{mrm}/f_{200}$ | | 0.46 | 0.92 | 0.38 | 1.32 | 0.67 | 0.4 |

We claim:

1. Acoustic attenuation device, comprising two substantially parallel plates defining a rectangularly shaped internal space therebetween, noise detection means arranged between the two plates, inverse noise emission means arranged between the two plates, and control means for controlling the inverse noise emission means in such a way as to minimize a quantity supplied by the noise detection means, wherein the inverse noise emission means comprise four actuators whose respective positions parallel to the plates correspond approximately to four points constituting the centers of respective sides of the rectangular shape of said internal space wherein the noise detection means comprise four sensors whose respective positions parallel to the plates correspond approximately to four points constituting the centers of respective sides of a rhombus whose vertices are the centers of the sides of the rectangular shape of said internal space, wherein the four actuators are controlled in phase, and wherein the quantity to be minimized is represented by the sum of the output signals of the four sensors.

2. Acoustic attenuation device, comprising two substantially parallel plates defining a rectangularly shaped internal space therebetween, noise detection means arranged between the two plates, inverse noise emission means arranged between the two plates, and control means for controlling the inverse noise emission means in such a way as to minimize a quantity supplied by the noise detection means, wherein the noise detection means comprise four sensors whose respective positions parallel to the plates correspond approximately to four points constituting the centers of respective sides of the rectangular shape of said internal space, wherein the inverse noise emission means comprise four actuators whose respective positions parallel to the plates correspond approximately to four points constituting the centers of respective sides of a rhombus whose vertices are the centers of the sides of the rectangular shape of said internal space, wherein the four actuators are controlled in phase, and wherein the quantity to be minimized is represented by the sum of the output signals of the four sensors.

3. Device according to claim 1, wherein the materials and the dimensions of the plates are chosen in such a way as to satisfy the relationships:

$f_c/(L_xL_y)^2>800$ and $f_{mrm}<f_{200}$ or the relationships $f_c/(L_xL_y)^2>300$ and $f_{mrm}<f_{200}/2$ in which $f_c$, expressed in hertz, denotes a critical frequency of a plate or the larger of two respective critical frequencies of the plates if the plates are of different compositions $L_x$ and $L_y$, expressed in meters, are the lengths of the sides of the rectangular shape of the internal space located between the two plates, $f_{mrm}$ is a resonant frequency of a mass-spring-mass system, constituted by the two plates and the medium located therebetween, and $f_{200}$ is an eigenfrequency given by the formula $f_{200}=c_0/\max(L_x, L_y)$, where $c_0$ denotes the speed of sound in the medium located between the two plates.

4. Device according to claim 1, further comprising a sensor supplying a reference signal, and a band-mass filter to which the reference signal is applied, the output of the bandpass filter being subjected to an adaptive filtering with finite impulse response in order to control the actuators, the band-pass filter allowing frequencies between $f_{mrm}/2$ and $\min(2 f_{mrm}, f_{200})$ to pass, where $f_{mrm}$ is a resonant frequency of a mass-spring-mass system constituted by the two plates and the medium located therebetween, and $f_{200}$ is an eigenfrequency given by the formula $f_{200}=c_0/\max(L_x, L_y)$, where $c_0$ denotes the speed of sound in the medium located between the two plates, and $L_x$ and $L_y$ denote the lengths of the sides of the rectangular shape of the internal space located between the two plates.

5. Device according to claim 1, wherein a gas lighter than air occupies the internal space located between the two plates.

6. Device according to claim 5, wherein said gas lighter than air is helium.

7. Device according to claim 2, wherein the materials and the dimensions of the plates are chosen in such a way as to satisfy the relationships:

$f_c/(L_xL_y)^2>800$ and $f_{mrm}<f_{200}$ or the relationships $f_c/(L_xL_y)^2>300$ and $f_{mrm}<f_{200}/2$ in which $f_c$ expressed in hertz, denotes a critical frequency of a plate or the larger of two respective critical frequencies of the plates if the plates are of different compositions $L_x$ and $L_y$, expressed in meters, are the lengths of the sides of the rectangular shape of the internal space located between the two plates, $f_{mrm}$ is a resonant frequency of a mass-spring-mass system, constituted by the two plates and the medium located therebetween, and $f_{200}$ is an eigenfrequency given by the formula $f_{200}=c_0/\max(L_x, L_y)$, where $c_0$ denotes the speed of sound in the medium located between the two plates.

8. Device according to claim 2, further comprising a sensor supplying a reference signal, and a band-pass filter to which the reference signal is applied, the output of the band-pass filter being subjected to an adaptive filtering with finite impulse response in order to control the actuators, the band-pass filter allowing frequencies between $f_{mrm}/2$ and $\min(2 f_{mrm}, f_{200})$ to pass, where $f_{mrm}$ is a resonant frequency of a mass-spring-mass system constituted by the two plates and the medium located therebetween, and $f_{200}$ is an eigenfrequency given by the formula $f_{200}=c_0/\max(L_x, L_y)$, where $c_0$ denotes the speed of sound in the medium located between the two plates, and $L_x$ and $L_y$ denote the lengths of the sides of the rectangular shape of the internal space located between the two plates.

9. Device according to claim 2, wherein a gas lighter than air occupies the internal space located between the two plates.

10. Device according to claim 9, wherein said gas lighter than air is helium.

11. An acoustic attenuation device comprising two substantially parallel plates defining a rectangularly shaped internal space therebetween, a plurality of noise sensors arranged between the two plates, a plurality of acoustic actuators arranged between the two plates, and control means for controlling the acoustic actuators so as to minimize a sum of output signals of the noise sensors, wherein the acoustic actuators are controlled in phase, and wherein material and dimensions of the two plates are chosen to satisfy at least one relationship selected from the group of relationships consisting of:

$F_c/(L_xL_y)^2>800$ and $f_{mrm}<f_{200}/2$, and $F_c/(L_xL_y)^2>300$ and $f_{mrm}<f_{200}/2$, wherein $F_c$, expressed in hertz, denotes one member selected from the group consisting of a critical frequency of one of the two plates and a larger of two respective critical frequencies of the two plates wherein the two plates are of different compositions, $L_x$ and $L_y$, expressed in meters, are lengths of sides of a rectangular shape of internal space located between the two plates, $f_{mrm}$ is a resonant frequency of a mass-spring-mass system, comprising the two plates and medium located therebetween, and $f_{200}$ is an eigenfrequency given by the formula $F_{200}=C_0/\max(L_x, L_y)$ where so denotes speed of sound in medium located between the two plates.

12. The device according to claim 11, further comprising a reference signal sensor supplying a reference signal, and a band-pass filter to which the reference signal is applied, the output of the band-pass filter being subjected to an adaptive filtering with finite impulse response in order to control the acoustic actuators, the band-pass filter allowing frequencies between $f_{mrm}/2$ and rain(2 $f_{mrm}$, $f_{200}$) to pass.

13. The device according to claim 11, wherein a gas lighter than air occupies internal space located between the two plates.

14. The device according to claim 13, wherein said gas lighter than air is helium.

15. An acoustic attenuation device comprising two substantially parallel plates defining a rectangularly shaped internal space therebetween, a plurality of noise sensors arranged between the two plates, a plurality of acoustic actuators arranged between the two plates, and control means for controlling the acoustic actuators so as to minimize a sum of output signals of the plurality of noise sensors and wherein the acoustic actuators are controlled in phase, reference signal sensor supplying a reference signal, and a band-pass filter to which the reference signal is applied, wherein output of the band-pass filter is subjected to an adaptive filtering with finite impulse response to control the acoustic actuators, the band-pass filter allowing frequencies between $f_{mrm}/2$ and $\min(2 f_{mrm}, f_{200})$ to pass, wherein $f_{mrm}$ is a resonant frequency of a mass-spring-mass system comprising the two plates and medium located therebetween, and $f_{200}$ is an eigenfrequency given by the formula $f_{200}=C_0/\max(L_x, L_y)$, where co denotes the speed of sound in medium located between the two plates, and $L_x$ and $L_y$ denote lengths of sides of a rectangular shape of internal space located between the two plates.

16. The device according to claim 15, wherein a gas lighter than air occupies internal space located between the two plates.

17. The device according to claim 16, wherein said gas lighter than air is helium.

* * * * *

UNITED STATES PATENT AND TRADEMARK OFFICE

CERTIFICATE OF CORRECTION

PATENT NO. : 5,724,432

DATED : March 3, 1998

INVENTOR(S) : Pascal BOUVET, Jacques ROLAND and Laurent GAGLIARDINI

It is certified that error appears in the above-indentified patent and that said Letters Patent is hereby corrected as shown below:

On the front page of the Letters Patent please delete the assignee name "Centre Scientifigue et Technique du Bâtiment" and insert --Centre Scientifique et Technique du Bâtiment--.

Signed and Sealed this

Sixth Day of October, 1998

Attest:

Bruce Lehman

BRUCE LEHMAN

*Attesting Officer* *Commissioner of Patents and Trademarks*